United States Patent
Govek et al.

(10) Patent No.: US 6,589,650 B1
(45) Date of Patent: Jul. 8, 2003

(54) MICROSCOPE COVER SLIP MATERIALS

(75) Inventors: Michael Govek, Minneapolis, MN (US); Babu N. Gaddam, Woodbury, MN (US); Cynthia M. Hogerton, White Bear Lake, MN (US); Audrey S. Huang, Woodbury, MN (US); Maureen A. Kavanagh, Stanchfield, MN (US); Junkang Liu, Woodbury, MN (US); Michael L. Ruegsegger, Mahtomedi, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 298 days.

(21) Appl. No.: 09/633,835

(22) Filed: Aug. 7, 2000

(51) Int. Cl.⁷ ............................ B32B 7/10; B32B 27/08; B32B 27/16; B32B 27/30; B32B 27/36
(52) U.S. Cl. .................. 428/355 AC; 428/13; 428/343; 428/346; 428/421; 428/446; 428/447; 428/483; 428/507; 428/510; 428/515; 428/520; 428/522; 156/57; 359/396; 359/397
(58) Field of Search ................. 428/343, 346, 428/355 AC, 480, 483, 421, 447, 446, 13, 507, 510, 515, 520, 522; 156/57; 359/396, 397

(56) References Cited

U.S. PATENT DOCUMENTS

| | | | |
|---|---|---|---|
| 2,532,011 A | 11/1950 | Dahlquist et al. | 154/53.5 |
| 3,498,860 A | 3/1970 | Pickett | 156/57 |
| 3,891,327 A | 6/1975 | Welch | 356/244 |
| 3,939,019 A | 2/1976 | Pickett | 156/57 |
| 4,077,830 A | 3/1978 | Fulwiler | 156/249 |
| 4,188,246 A | 2/1980 | Lipshaw | 156/57 |
| 4,203,797 A | 5/1980 | Stormby | 156/521 |
| 4,455,188 A | 6/1984 | Stormby | 156/355 |
| 4,853,262 A | 8/1989 | Horie et al. | 428/13 |
| 5,104,929 A | 4/1992 | Bilkadi | |
| 5,332,797 A | 7/1994 | Kessel et al. | 528/27 |
| 5,506,279 A | 4/1996 | Babu et al. | 522/34 |
| 5,677,050 A | 10/1997 | Bilkadi et al. | 428/331 |
| 5,712,325 A * | 1/1998 | Lewis et al. | 428/412 |
| 5,811,472 A * | 9/1998 | Patel | 522/14 |
| 5,812,312 A | 9/1998 | Lorincz | 359/397 |

FOREIGN PATENT DOCUMENTS

| | | |
|---|---|---|
| CH | 400607 A | 4/1966 |
| EP | 0 278 060 A2 | 8/1988 |
| EP | 0 797 111 A2 | 9/1997 |
| FR | 2542876 | 9/1984 |
| JP | 11101943 | 4/1999 |
| WO | WO 99/37720 A1 | 7/1999 |
| WO | WO99/53357 | 10/1999 |
| WO | WO 99/57375 A1 | 11/1999 |
| WO | WO 99/64899 A1 | 12/1999 |

* cited by examiner

Primary Examiner—Vivian Chen
(74) Attorney, Agent, or Firm—Robert W. Sprague

(57) ABSTRACT

A cover slip material and a method of making and using the same are provided. The material comprises (a) a light transmissible polymeric backing having first and second surfaces; (b) a tack free bonding layer disposed on the first surface of the backing, the bonding layer comprising polymers selected from the group consisting of acrylate, methacrylate, and combinations thereof; and (c) a protective coating disposed on the second surface of the backing. Upon exposure to an environmentally friendly activating solvent such as terpene, d-limonene, esters of coconut oil and aliphatic hydrocarbon blends, the bonding layer acquires tacky properties causing the cover slip to adhere to a specimen previously mounted on a microscope slide.

18 Claims, 1 Drawing Sheet

MICROSCOPE COVER SLIP MATERIALS

TECHNICAL FIELD

This invention relates generally to polymeric cover slip materials useful for storing biological specimens for a prolonged period of time. In particular, the cover slip material contains a bonding layer that, when activated with a solvent, exhibits adhesive properties and seals the specimen for later use.

BACKGROUND

In the biological disciplines such as histology or microbiology, it is a common practice to examine a specimen, such as tissue samples, using a microscope, such as a light microscope. Such a practice requires mounting the specimen on a slide, typically a glass slide. A cover slip can be used to protect the specimen and microscope lens. Thin light transmissible glass slides have been used as cover slips. The disadvantage with using glass slides is that they typically cannot preserve the specimen, are fragile, and thus susceptible to fracture thereby possibly damaging the specimen and injuring the user.

In the case where the specimen needs to be preserved for later examination and viewing, some skilled in the art have sealed the cover slip to the slide. For example, U.S. Pat. No. 4,853,262 (Horie et al.) discloses cover film for use in microscopy. The film comprises a plastic substrate and a polymer adhesive disposed thereon. The adhesive is a blend of a first polymer adhesive, having a $T_g$ of at least 80° C. (176° F.), and a second polymer adhesive, having a $T_g$ of at least 50° C. (122° F.). The first and second adhesives are different and they can be selected from the group consisting of acrylic adhesive and acrylic copolymer of alkyl methacrylate and alkyl acrylate. The polymer adhesive preferably dissolves or at least swells in an organic solvent, such as xylene.

Others skilled in the art have explored different methods of providing a sealing agent that can be activated in an applying machine, or at the time the cover slip is applied to the slide, by application of a solvent. See, e.g., U.S. Pat. Nos. 4,455,188; 4,188,246; and 3,939,019.

U.S. Pat. No. 3,891,327 (Welch) discloses a method of securing specimen between a cover glass and a glass slide. The method involves (1) covering the glass slide in the region of the specimen with a liquid photosensitive composition consisting essentially of an optically transparent liquid photosensitive material and a photoinitiator, (2) positioning the cover glass over the specimen in contact with the photosensitive composition, and (3) exposing the photosensitive composition to ultraviolet radiation. This process yields a sample where the cover glass and the specimen are in a fixed position on the glass slide. A useful photosensitive composition consists essentially of an acrylate, methacrylate or mixtures thereof and a photoinitiator.

WO 99/53357 discloses a combination comprising (1) a slide suitable for optical microscopy to which a specimen has been applied, and (2) an optically transparent cover adhered to the slide over the specimen. The cover comprises an optically transparent polymeric film with opposite first and second major surfaces, and a contact responsive adhesive on the first major surface, which is in contact with the slide. In some embodiments of the invention, a wetting agent can be applied to the cover or the specimen before the cover is adhered to the slide to improve viewing of the specimen. The contact responsive adhesive is described as pressure sensitive adhesive that adheres relatively quickly and strongly to the target surface yet exhibits essentially no surface tack to the skin when coated on the optically transparent polymeric film.

While the foregoing cover slips are useful, other cover slip compositions are sought.

SUMMARY OF INVENTION

The present invention provides for a new and improved cover slip material. The inventive cover slip materials possess desirable features, such as clarity, refractive index similar to that of the slide, quick interaction with the activating solvents, compatibility with the staining chemicals used on specimens, and improved stability to high temperature, high humidity conditions for prolonged periods of time.

In one aspect, the invention provides for a flexible, light transmissible cover slip comprising or consisting essentially of (a) a light transmissible polymeric backing having first and second surfaces; (b) a tack free bonding layer disposed on the first surface of the backing, the bonding layer comprising polymers selected from the group consisting of alkyl acrylate, alkyl methacrylate, and combinations thereof; and (c) a protective coating disposed on the second surface of the backing.

In another aspect, the invention provides a method for preparing an optical microscopy slide comprising (a) placing a specimen on a slide, (2) covering the specimen with a flexible cover slip comprising (i) an optically transparent polymeric backing having first and second surfaces; (ii) a substantially tack free bonding layer disposed on the first surface of the backing, the bonding layer comprising polymers selected from the group consisting of alkyl acrylate, alkyl methacrylate, and combinations thereof, (iii) a protective coating disposed on the second surface of the backing; and (3) applying an activating solvent to the bonding layer, wherein upon exposure to the activating agent, at least a portion of the bonding layer is dissolved and the cover slip adheres to the specimen and the microscope slide to yield a prepared slide.

The present invention is unlike the invention disclosed in WO 99/53357 in several respects. First, whereas WO 99/53357 may use a wetting agent on the cover or the specimen before the cover is adhered to the slide to improve viewing of the specimen, the present invention uses an activating solvent to at least partially solvate the bonding layer to impart pressure sensitive adhesive properties. Second, the adhesive system disclosed in WO 99/53357 is described as being contact responsive adhesives and are pressure sensitive adhesives. Such adhesives are described as capable of adhering relatively quickly and strongly to the target surface, i.e., the slide and specimen mounted thereon. The present invention, on the other hand, uses a solvent to activate the bonding layer so as to impart to it adhesive properties allowing it to bond to the target surface. The bonding layer of the present invention is not a contact responsive adhesive.

An advantage of the present invention is that the bonding layer can be solvated in a variety of activating solvents, some of which are environmentally friendly and pose less health hazard to people. These environmentally friendly solvents include, e.g., d-limonene (diterpene-based material), coconut oil ester, aliphatic hydrocarbon blends, and petroleum distillates.

Another advantage of the present invention is that the cover slip can withstand high temperature and high humidity conditions for a prolonged period of time, as further described herein, without adversely affecting the specimen. As a result of the performance, the specimen can be preserved for a longer period of time.

A tack-free bonding layer would have a tack value of less than 2, preferably 1.5 and lower, most preferably 0.5 and lower before activation. It would have little to no (i.e., less than 0.5 N/25 ohm, preferably nearly 0) adhesion to glass before activation, as measured according to ASTM D-333D, described below.

In yet another advantage of the invention, the bonding layer is initially tack-free, meaning that it has little to no adhesion to most substrates, such as the slide, the equipment parts used to perform cover slip operations, skin, and gloves until it is activated. Upon exposure to an activating solvent, the bonding layer quickly acquires tack and adheres to the specimen and slide.

BRIEF DESCRIPTION OF THE DRAWINGS

The invention will be further described with reference to the drawing wherein.

Figure 1:
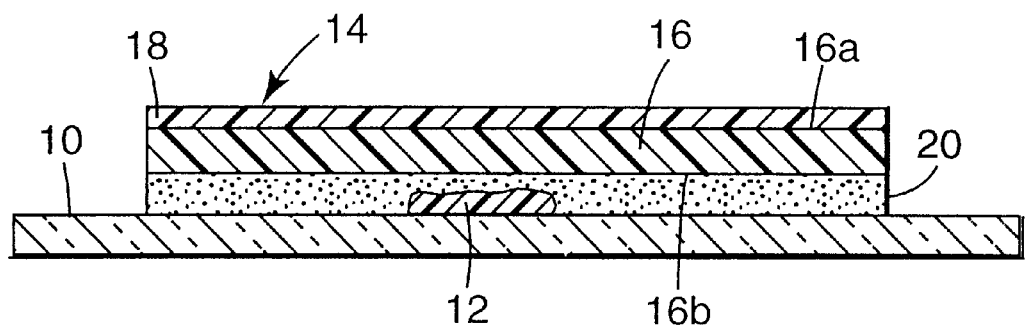
FIG. 1 is a cross-sectional view of one embodiment of the invention containing microscope slide 10 with a specimen 12 mounted thereon. A cover slip 14 is disposed on the specimen and at least a portion of the slide. The cover slip 14 has a backing having a first surface 16a and a second surface 16b. A protective coating 18 is disposed on at least a portion of surface 16a. A bonding layer 20 is disposed on at least a portion of surface 16b.

These figures are idealized, not drawn to scale, and are intended merely to be illustrative and non-limiting.

DETAILED DESCRIPTION OF THE INVENTION

The present invention provides a new and improved cover slip useful for numerous microscopy applications, particularly in the histology and biology fields. The cover slip contains a backing, a bonding layer, and a protective coating. Each component is described below in detail.

Preferably, the refractive index ($N_D$) of the components of the cover slip 14 are near the $N_D$ of the slide 10, typically a glass microscope slide. Commercially available glass slides typically have a $N_D$ of approximately 1.51, and preferred materials for use in the cover have refractive indices that approximate this value. Accordingly, preferred materials have refractive indices of at least 1.45, and more preferably of at least 1.47. While materials having a refractive index as high as 1.65 are considered useful, materials with refractive indices between about 1.47 and 1.55 are most preferred.

Because the total transmission of light through the cover slip must be adequate to ensure that sufficient light reaches the eye or camera viewing the specimen, the luminous transmittance of light (measured according to ASTM D1003-95) through the cover should be maximized. The cover should possess a luminous transmittance of at least about 85%, and more preferably at least about 94%. Accordingly, the luminous transmittance of the cover slip components (e.g., light transmissible polymeric backing) should be selected to maximize luminous transmittance and preferably the total transmittance of each component of the cover is at least 85%.

The backing is a light transmissible polymer film, preferably having a thickness between about 100 to 250 micrometers. A thickness within this range provides good flexibility for use in roll form with automated application systems while maintaining sufficient strength for processing. Suitable films for use as backings include polymethyl methacrylate, polyethylene terephthalate, styrene-acrylonitrile copolymer, cellulose diacetate, and cellulose triacetate. One particularly preferred material is film made from polymethyl methacrylate resin that is commercially available as V045-UVA10-100 from Atohaas Americas, Inc. of Philadelphia, Pa. The backing can be made by conventional extrusion of the polymethyl methacrylate resin into a film and optionally orienting the film uniaxially or biaxially.

The backing can be treated by corona, such as air or nitrogen corona, plasma flame, or actinic radiation to improve the bonding between it and the bonding layer. Such treatment can also be used to improve bonding between the backing and the protective coating. If desired, a tie layer can be used between the backing and the bonding layer as well as between the backing and the protective coating to increase the adhesion of the layers. A bonding layer is disposed on one major surface of the backing.

The bonding layer initially has little to no tack and is not a pressure sensitive adhesive (PSA). This initial lack of PSA properties allows the cover film to be processed through the automated cover slip machines without sticking to the various parts of the machine. Upon exposure to an activating solvent, the bonding layer at least partially solvates (i.e., dissolves) and becomes tacky so as to adhere to the target surface, i.e., the specimen and the microscope slide.

A PSA typically has tack at room temperature, requires moderate pressure to achieve a bond (such as that exerted by fingertip pressure), and adheres to a wide variety of dissimilar substrates. A PSA is conventionally understood to refer to an adhesive that displays permanent and aggressive tack to a wide variety of substrates after applying moderate pressure. An accepted quantitative description of a PSA is given by the Dahlquist criterion line, which indicates that materials having a storage modulus (G') of less than about $3 \times 10^5$ Pascals (measured at 10 radians/second at a temperature of about 20° C. to 22° C. (68° F. to 71.6° F.) have PSA properties while materials having a G' in excess of this value do not.

Suitable polymers for use as the bonding layer include polymers of alkyl acrylate and alkyl methacrylates. Useful alkyl acrylates include n-butyl acrylate, 2-ethylhexyl acrylate, isooctyl acrylate, isononyl acrylate, isobornyl acrylate, t-butylacrylate and octadecyl acrylate. Useful alkyl methacrylates include cyclohexyl methacrylate and isobornyl methacrylate. The polymers of alkyl acrylate and alkyl methacrylates can be used as a homopolymers or as copolymers.

In one embodiment, the bonding layer comprises at least 65 wt. percent of class A polymer and at most 35 wt. percent of class B polymers. Suitable class A polymers include isobornyl acrylate, isobornyl methacrylate, cyclohexyl methacrylate, t-butyl acrylates, and octadecyl methacrylate. Suitable class B polymers include 2-ethylhexyl acrylate, isooctyl acrylate, isononyl acrylate, and n-butyl acrylate. In a preferred embodiment, the bonding layer comprises two alkyl acrylates, isobornyl acrylate and 2-ethylhexyl acrylate, in a weight ratio of about 65:35 to 90:10. In another embodiment, the bonding layer comprises octadecyl acrylate and 2-ethylhexyl acrylate in a weight ratio of about 65:35 to 90:10. In yet another embodiment, the bonding layer comprises cyclohexyl methacrylate and 2-ethylhexyl acrylate in a weight ratio of 65:35 to 90:10. In yet another embodiment, the bonding layer comprises two alkyl acrylates, isobornyl acrylate and n-butyl acrylate, in a weight ratio of about 65:35 to 90:10. Thus, unlike the prior art, the inventive bonding layer is not a blend of two polymer adhesives.

The bonding layer can be made by various methods, such as by solution polymerization or by photopolymerization. In solution polymerization, the alkyl acrylates and/or alkyl methacrylates are typically charged into a vessel, along with solvents, such as ethyl acetate, and a thermal initiator or a polymer catalyst, such as 2,2'-azobisisobutyronitrile. If desired, heat can be used. The resulting solution can be coated on to a polymeric web and dried, usually in a forced air oven, to form the bonding layer. In photopolymerization, a photoinitiator, such as the IRGACURE series from Ciba Specialty Chemicals, can be added to a mixture containing the alkyl acrylates and/or alkyl methacrylates. The mixture can be coated on to the polymer backing and cured using a UV light energy source. If desired, in either polymerization methods, chain transfer agents, such as carbon tetrabromide and isooctylthioglycolate, can be used to control the molecular weight of the coating solution or mixture.

The bonding layer can be crosslinked with various agents to increase the internal cohesive strength and to reduce the rate of dissolution of the bonding layer in the activating agent, particularly when a xylene activating agent is used. Suitable crosslinking agents include diacrylates, such as 1,6-hexanediol diacrylate (HDDA), 1,4 butanediol diacrylate, and others. When used, the crosslinking agent is present in about less than about 1 part, preferably less than about 0.2 parts, more preferably less than about 0.05 parts by weight.

The bonding layer is preferably light transmissible. The bonding layer can be solvated in numerous activating solvents, including xylene, toluene, d-limonene, esters of coconut oil, aliphatic hydrocarbon blends, and petroleum distillates. Preferably, the bonding layer is solvated within a short period of time, e.g., within 30 seconds, more preferably within about 15 seconds, most preferably within about 5 seconds.

The inventive cover slip, when used on the microscope slide, preferably can withstand exposure to high humidity and high temperature for a prolonged period of time without significant lifting of the cover slip material from the microscope slide and without significant bleeding and/or fading of the stained specimen. For example, preferred cover slip materials can withstand humidity of greater than about 50%, preferably greater than about 60%, and more preferably greater than about 75%, most preferably greater than about 90% relative humidity at elevated temperatures of greater than about 26.7° C. (80° F.), preferably greater than about 37.8° C. (100° F.), more preferably greater than about 48.9° C. (120° F.) for a prolonged period of time, preferably greater than about 3, more preferably greater than 5 days, most preferably greater than 7 days.

The bonding layer, during storage of the tissue sample and even under solvent activation, preferably does not interact with the various stains used to stain the biological tissues, such as hematoxylin and eosin (H-E stain). By "not interact," it is meant that the bonding layer, and/or the solvents used to activate it, does not cause the stain to bleed or fade.

A bonding layer that includes methyl methacrylate and/or benzoyl acrylate does not yield a cover slip with desired properties. For example, a bonding layer that uses methyl methacrylate is not activated by the environmentally friendly activators, such as d-limonene, among others. A bonding layer that contains benzoyl acrylate tends to exhibit too much initial tack.

The inventive cover slip material contains a protective coating disposed on one side of the polymer backing. The protective coating serves several purposes. For example, it functions as a release coating to prevent blocking during wind-up. It provides solvent resistance to protect the polymer backing from the activating solvents and optionally scratch resistance. Blocking, an undesirable feature, means generally that the bonding layer is at least partially adhered to both side of the polymer backing causing extra unwinding force and/or causing the bonding layer to split upon unwinding.

In one preferred embodiment, the inventive cover slip material containing the backing, bonding layer, and protective layer is wound up in roll form. The roll can be placed under high temperature conditions, about 49° C. (120° F.) for about ten weeks without blocking. More preferably, the roll can withstand 49° C. conditions for at least seven days.

Preferably, the protective material has write-ability features, meaning that it accepts markings from writing utensils, such as pens, markers, and the like. Also, the protective coating preferably has desirable optical properties, such as greater than about 85%, more preferably greater than about 90% transmission of light; less than 5%, preferably less than about 3%, most preferably less than 1% haze; and greater than about 90%, preferably greater than about 95%, more preferably greater than about 99% clarity. The transmission of light and haze are measured according to ASTM D-1003. Clarity is measured according to the test methods described in the manual for the Hazeguard™ Plus, (Cat. No. 4725, available from BYK-Garner USA, Silver Spring, Md.).

Suitable materials for use as protective coatings are silicone-based, fluorosilicone-based materials, fluorochemical-based materials, fluoroether-based materials, ceramer materials, and combinations thereof. For example, a protective coating could contain a fluorochemical, a silicone, and a ceramer.

Illustrative examples of components that can be used to formulate silicone-based protective coatings include, e.g., (1) silanol terminated polydimethylsiloxane, such as DMS-S12 from Gelest Company, Tullytown, Pa., (2) 1,8-bistriethoxysilyl octane, such as SIB 1824 from Gelest, (3) 3-triethoxysilylpropyl acrylate, and (4) silicone acrylate, such as RC 706, RC 711, RC 726, RC 902, and mixtures thereof, from Goldschmidt Company, Hopewell, Va., which are believed to be about 5000 molecular weight methacrylate-silicone having pendant-type acrylates, (5) epoxy-silicone, such as product number UV 9430 from General Electric Co., Waterford, N.Y. and a mixed epoxy silicone having an equivalent weight of about 530. The mixed epoxy silicone can be made by hydrosilylation of polymethylhydrosiloxane with allyl glycidyl ether and 4-cylcohexeneoxide. U.S. Pat. No. 5,332,797 discloses a method of making epoxy silicone.

Illustrative examples of components that can be used to formulate a fluorosilicone-based protective coatings include, e.g., (1) 1,1,2,2-tetrahydrotridecafluorooctyl-triethoxysilane (common name, tridecafluorooctyltriethoxysilane), such as SIT 8175 from Gelest, and (2) 1,1-dihydroheptafluorobutyl acrylate, such as product 14360-2 from PCR Inc., Gainesville, Fla. These components are typically used in conjunction with the silicone-based components listed above.

Illustrative examples of components that can be used to formulate fluoroether-based protective coatings include, e.g., (1) fluoroether-diacrylate solution in HFE 7200, and (2) fluoroether-disilane solutions. The fluoroether-disilane can be made from the reaction of fluoroether diester (e.g., Fomblin product available from Aunsimont Co., Bollate, Milan, Italy) with 3-aminopropyltriethoxysilane.

The ceramer materials provide scratch and solvent resistance. The preferred ceramers are those described in U.S. Pat. No. 5,677,050, which discloses a composition comprising about 20% to 80% ethylenically unsaturated monomers, about 10% to 50% acrylate functionalized colloidal silica, and about 5% to 40% N,N-disubstituted acrylamide monomer or N-substituted-N-vinyl-amide monomer. The percentages are weight percents of the total weight of the composition. More preferably, the ceramer formulation contains about 60% reactive solids in an isopropanol solvent. The solids contain about 22 to 27% by weight acrylate functionalized colloidal silica, about 20 to 25% by weight pentaerythritol tetraacrylate, about 7 to 12% by weight penta erythritol triacrylate, about 5 to 10% by weight acrylate esters, and about 3 to 8% by weight N,N-dimethyl acrylamide.

A preferred protective coating contains a hybrid between the silicone-based material and the ceramer. In one preferred embodiment, the ceramer is combined with silicone acrylate to yield the protective coating, wherein the ceramer is greater than 70% by weight and less than 30% by weight silicone acrylate.

The protective coating formulation is typically in liquid form and made by mixing various combinations of components, described above, with initiators, and, optionally, solvents. Illustrative example of useful initiators include (1) photo acid, such as RHODORSIL 2074 from Rodia Inc., Rock Hill, S.C., and (2) photo radical initiator, such as DAROCURE 1173 and IRGACURE 184, from Ciba Specialty Chemicals, Tarrytown, Pa.

The liquid protective coating is applied to the substrate by conventional coating methods, such as gravure, notch-bar, reverse roll, or curtain coating. Gravure coating is the preferred method as it can apply a thin layer, on the order of 1 to 5 micrometers in wet thickness. The wet coating is dried, typically using forced air ovens. The dried coating can be further cured and crosslinked using an energy source. Useful energy sources include ultraviolet light curing devices using a UV "C" dosage of about 30 to 60 milliJoules per square centimeter ($mJ/cm^2$). Presently, it is preferred that the cure step occurs in an environment containing low amounts of oxygen, e.g., less than about 100 parts per million. Typically, the environment is filled with nitrogen gas.

Methods of Making

The cover slip material can be made by providing a substrate having two major surfaces, applying the protective coating to the first major surface, and applying the bonding layer to the second major surface. The steps can be done simultaneously, in series, or as separate steps.

The presently preferred method is to process the protective coating first and wind-up the product in roll form. During wind-up, the cured and dried protective coating contacts the backside of the substrate. In some protective coating formulations, such as those containing silicone-based components, there may be transfer of the components. In one embodiment, the backside of the substrate functions as the coating surface for the bonding layer. If any components should transfer, the type and amount of transfer preferably should not adversely affect the bonding layer coating and processing steps and should not affect the adhesion of the bonding layer to polymeric backing. One method to minimize, if not eliminate, the transfer is to use a slip sheet so as to sandwich the protective coating between the substrate and the slip sheet.

The bonding layer is applied to the substrate by various coating methods, depending on its nature. The bonding layer can be a solvent cast system, in which case it can be coated to the substrate using coating methods listed above for the protective coating. In this case, the bonding layer would be dried, usually in a forced air oven, and cured, either in a forced air oven or through some other energy source. The bonding layer can be a substantially solventless system, in which case it can be photopolymerized and cured. The thickness of the bonding layer is in the range of about 10 to 100 micrometers, preferably about 20 to 50 micrometers.

EXAMPLES

The following examples further illustrate various specific features, advantages, and other details of the invention. The particular materials and amounts recited in these examples, as well as other conditions and details, should not be construed in a manner that would unduly limit the scope of this invention. Percentages given are by weight, unless otherwise specified.

Test Methods

Tack Testing

The tack of the inventive bonding layer was qualitatively assessed by a "finger appeal" test involving a light touch and short contact time, and assigned a value of 0 through 5, where 0=tack free, 0.5=very, very low tack, 1=very low tack, 1.5=low tack 2=low-to-medium tack, 3=medium tack, 4=high tack, and 5=very high tack. On this scale, Post-It® Notes and SCOTCH MAGIC transparent tape, both available from Minnesota Mining and Manufacturing Co. (3M), St. Paul, Minn., USA have ratings of 2 and 5, respectively.

Accelerated Aging Testing

A selected number of Examples below were subjected to accelerated testing as follows: We obtained histology slides that contain a stained specimen mounted on a glass microscope slide. The histology slides were stored in a rack immersed in a xylene bath until ready for use. The inventive cover slip material was applied to the histology slides using a Tissue-Tek® SCA™ cover slipper, available from Sakura Finetek, USA, Inc., Torrance, Calif. The cover slipped microscope slides were then placed in a rack and placed in a chamber set at about 49° C. (120° F.), about 90% relative humidity, for about 7 days. One chamber used is available from Environmental Chamber, Forma Scientific Division of Mallinckrodt, Inc., Marietta, Ohio, model number 4940. After this duration, the slides were removed and were visually rated as either "pass" or "fail." A "pass" means very little lifting (about 1 to 2 mm and at most 5 mm) of the cover slip from the microscope slide. The lifting is typically limited to the edges of the cover slip material. Very slight bubbling of the cover slip material, on the order of less than 10, preferably less than 5 bubbles having diameters of less than about 2 to 3 mm, are allowed. Very little bleeding or fading of the stain is allowed. A "fail" rating means substantial lifting of the cover slip material. Not only edge lifting but also lifting over the specimen would be classified as a "fail." Numerous and large bubbles, greater than about 4 mm in diameter, in the cover slip would be considered a "fail." Typically, when this test is used, a "control sample" containing a glass cover slip was used for comparison purposes.

Adhesion to Glass

Adhesion of the cover slip material to glass was measured using 180° peel adhesion. The testing was essentially according to ASTM D-3330, using a model SP101B testing machine with type SPM-04 modifications (commercially available from IMASS of Hingham, Mass.), except that a glass target surface and a peel rate of 229 cm/min were used. The results are reported in units of Newtons per 25 millimeter width (N/25 mm width).

Examples 1 to 15

These Examples show the components of various protective coatings formulations. In Table 1 below, the components used to make the coatings are categorized. Within each category, the amount and type of material are listed. For example, "DMS-S12" is silanol terminated polydimethylsiloxane, "SIB 1824" is 1,8-bistriethoxysilyl octane, "TESPA" is 3-triethoxysilylpropyl acrylate, "RC 706," "RC 726", "RC 711," and "RC 902" are silicone acrylates, "SIT 8175" is tridecafluorooctyltriethoxysilane, "RHODOSIL" is RHODOSIL 2074—a photoacid, "DAROCURE" is DAROCURE 1173—a photo radical initiator, "DPTMBPO" is diphenyl trimethylbenzoyl phosphine oxide, and "IPA" is isopropanol.

The components listed in each Example were charged and mixed in a vessel. The mixture was coated on a PMMA backing, dried for about 2 minutes in a 70° C. (158° F.) oven, then cured in a nitrogen filled chamber equipped with an ultraviolet lamp unit containing a UV processor with a P300 power supply, and H bulbs. The UV processor was from Fusion UV Curing Systems, Rockville, Md.

In Examples 1 to 6 and 8, the coating apparatus used was a 5 roll coater. In Example 7, the coating apparatus used was a gravure coater. In Examples 9 to 15, the coating method used was a Meyer rod. In all Examples, the dry coating thickness was about 0.1 to 0.5 micrometer.

In all Examples, the backing used was extruded and oriented PMMA film made by Minnesota Mining and Manufacturing Company (3M), St. Paul, Minn. using PMMA resin V0-45-UVA10-100, supplied by Atohaas Americas, Inc., Philadelphia, Pa.

terephthalate film coated with polyvinylidene chloride latex primer. The coated solution was dried for about 10 minutes in a 65° C. oven to yield a cover slip having a bonding layer dry thickness of about 30 micrometers. The cover slip material was subjected to tack, adhesion to glass, and accelerated testing.

In Table 2 below, the components listed include alkyl acrylates, such as 2-ethylhexyl acrylate (2-EHA), isobornyl acrylate (IBOA), t-butyl acrylate (t-BA), and n-butyl acrylate (n-BA), and alkyl methacrylates, such as cyclohexyl methacrylate (CHMA).

TABLE 1

| Example | Silicone-based | Fluorosilicone-based | Fluoroether-based | Epoxy-based | Ceramer | Solvents | Photoinitiator | UV Dosage (mJ/cm$^2$) |
|---|---|---|---|---|---|---|---|---|
| 1 | 70 g DMS-S12 30 g SIB 1824 | 0 | 0 | 0 | 0 | 0 | 1 g RHODORSIL | 16 |
| 2 | 70 g DMS-S12 30 g SIB 1824 30 g TESPA | 0 | 0 | 0 | 0 | 1.2 g DPTMBPO | 1 g RHODORSIL | 16 |
| 3 | 100 g RC 706 | 0 | 0 | 0 | 0 | 0 | 2 g DAROCURE | 16 |
| 4 | 70 g DMS-S12 30 g SIB 1824 | 10 g SIT 8175 | 0 | 0 | 0 | 0 | 1 g RHODORSIL | 8 |
| 5 | 70 g DMS-S12 30 g SIB 1824 30 g RC 706 | 10 g SIT 8175 | 0 | 0 | 0 | 1.2 g DPTMBPO | 1 g RHODORSIL | 16 |
| 6 | 50 g RC 706 | 50 g HFBA | 0 | 0 | 0 | 0 | 2 g DAROCURE | 20 |
| 7 | 0 | 0 | 1% fluoroether-diacrylate[a] | 0 | 0 | 0 | 0 | 40 |
| 8 | 0 | 0 | 100 g fluoroether-disilane | 0 | 0 | 0 | 1 g RHODORSIL | 16 |
| 9 | 0.1 g RC 706 | 0 | 0 | 0 | 1 g | 10 g IPA | 0.04 g IRGACURE | 40 |
| 10 | 0.1 g RC 711 | 0 | 0 | 0 | 1 g | 10 g IPA | 0.04 g IRGACURE | 40 |
| 11 | 0.1 g RC 926 | 0 | 0 | 0 | 1 g | 10 g IPA | 0.04 g IRGACURE | 40 |
| 12 | 0.1 g RC 726 | 0 | 0 | 0 | 1 g | 10 g IPA | 0.04 g IRGACURE | 40 |
| 13 | 0.1 g MAUS | 0 | 0 | 0 | 1 g | 10 g IPA | 0.04 g IRGACURE | 40 |
| 14 | 0 | 0 | 0 | 0.1 g MES | 1 g | 10 g IPA | 0.04 g DAROCURE | 60 |
| 15 | 0 | 0 | 0 | 0.1 UV 9430 | 1 g | 10 g IPA | 0.04 g DAROCURE 0.01 g (RPh)$_2$ISBF$_6$ | 60 |

Example 16 to 17

These Examples show protective coatings containing perfluorooctyl acrylate.

In Example 16, 1 g ceramer solution, 0.1 g 1H, 1H-dihydroperfluorooctyl acrylate, 0.04 g DAROCURE 1173, and 10 g IPA were charged and mixed in a vessel. The resulting mixture was coated onto oriented PMMA from 3M using a Meyer rod. The coating was dried and cured as in Example 1, using a UV dosage of about 40 mJ/cm$^2$.

In Example 17, 1 g ceramer solution, 0.0 g RC 711, 0.05 g 1H, 1H-perfluorooctyl acrylate, 0.04 g DAROCURE 1173, and 10 g IPA were charged and mixed in a vessel. The resulting mixture was coated onto oriented PMMA from 3M using a Meyer rod. The coating was dried and cured as in Example 1, using a UV dosage of about 40 mJ/cm$^2$.

Examples 18 to 21

The following Examples show the various bonding layers made by solution polymerization.

The components listed in each Example in the amount listed in Table 2, along with 150 g ethyl acetate and 0.125 g 2,2'-azobisisobutyronitrile, were charged into glass bottles. The bottles were capped and placed for about 21 hours in a 60° C. (140° F.) water bath equipped with agitation to yield various copolymer solutions. Using a knife coater, the solutions were coated on 100 micrometer thick polyester

Comparative Example A

Into a glass bottle was charged 150 g ethyl acetate, 0.125 g 2,2'-azobisisobutyronitrile, 15 g 2-EHA, and 35 g methylmethacrylate. The bottles were capped and the solution was processed according to Example 18. The resulting cover slip material was subjected to the testing listed in Table 2, and had a tack value of 0.5, an adhesion to glass value of 0, and failed the accelerated testing because there were numerous bubbles, many of which were substantial in size.

TABLE 2

| Solution Polymerization of Bonding Layer | | | | |
|---|---|---|---|---|
| Monomer | 18 | 19 | 20 | 21 |
| 2-EHA (g) | 10.0 | 10.0 | 10.0 | 0 |
| n-BA (g) | 0 | 0 | 0 | 10.0 |
| IBOA (g) | 40.0 | 0 | 0 | 40.0 |
| t-BA | 0 | 40.0 | 0 | 0 |
| CHMA (g) | 0 | 0 | 40.0 | 0 |
| Results: | | | | |
| Tack (rating) | 1 | 1.5 | 0.5 | 0.5 |
| Adhesion to glass (N/25 mm width) | 0 | 0 | 0 | 0 |
| Accelerated aging | P | P | P | P |

Examples 22 to 28

The following Examples show the various bonding layers made by photopolymerization.

A series of bonding layers were made by first partially polymerizing a mixture of 2-EHA, IBOA, and ODA monomers according to Table 3. For each 100 parts by weight (pbw) of monomer, about 0.04 pbw of IRGACURE 2959, available from Ciba Specialty Chemicals, Tarrytown, N.Y. was used. The partial photopolymerization was done in an inert (nitrogen filled) atmosphere using a bank of 40-watt fluorescent backlights to provide a coatable mixture.

Following the partial photopolymerization, about 0.16 pbw of DAROCURE 1173, available from Ciba Specialty Chemicals, was added to the mixture.

In the Examples, the mixture was knife coated on 100 micrometer thick PET film and exposed under a bank of lights providing an irradiated dose of about 930 mJ/cm$^2$. The PET film contained a coating of polyvinylidene chloride latex primer.

In all examples, the coating and irradiating steps were done in an inert (i.e., nitrogen filled) chamber.

TABLE 3

Photopolymerization of Monomers to Yield Bonding Layers

| Monomer | 22 | 23 | 24 | 25 | 26 | 27 | 28 |
|---|---|---|---|---|---|---|---|
| 2-EHA (g) | 52.5 | 45.0 | 37.5 | 30.0 | 22.5 | 15.0 | 20 |
| IBOA (g) | 97.5 | 105.0 | 112.5 | 120.0 | 127.5 | 135.0 | 0 |
| ODA | 0 | 0 | 0 | 0 | 0 | 0 | 80 |
| Results: | | | | | | | |
| Tack (rating) | 0.5 | 0 | 0 | 0 | 0 | 0 | 1 |
| Adhesion to glass (N/25 mm width) | 0 | 0 | 0 | 0 | 0 | 0 | 0 |
| Accelerated aging | P | P | P | P | P | P | P |

Comparative Example B

A bonding layer was made according to Example 22, except that 40 g of 2-EHA and 60 g of IBOA were used as monomers. About 0.001 g of 1,6-hexanediol diacrylate (HDDA) and about 0.02 g of carbon tetrabromide (CBr$_4$) were used. The latter was used as a chain transfer agent. The mixture was knife-coated on to 120 micrometer thick oriented PMMA film and cured under a bank of lights providing an irradiated dose between 870 and 885 mJ/cm$^2$. The resulting cover slip material was subjected to tests listed in Table 3, and had a tack value of 2. The cover slip material had a high adhesion to the glass. Also, the bond strength was greater than the strength of PMMA backing and thus could not be determined using the 180° peel test. Because of this result, the sample was not subjected to accelerated aging testing.

Comparative Example C

A bonding layer was made according to Example 22, except that 52 g 2-EHA, 20 g IBOA, and 28 g N-vinyl caprolactam were used as monomers. The mixture was knife-coated on to 120 micrometer thick oriented PMMA film and cured under a bank of lights providing an irradiated dose between 870 and 885 mJ/cm$^2$. The resulting cover slip material was subjected to tests listed in Table 3, and had an adhesion to glass of 1.25N/25 mm width, which would be considered unacceptably high. The cover slip material failed the accelerated aging test as the hematoxylin and eosin stain bled into the cover slip material.

Example 29

A cover slip film was made as follows. The protective coating of Example 9 was coated and processed as described on a first side of a 0.005 inch (0.12 mm) oriented PMMA film. The bonding layer, made according to Example 22 but containing 20 g 2-EHA, 80 g IBOA and 0.001 g HDDA was coated and processed as described on a second side of the PMMA film.

The cover slip material was activated by each of the following solvents: xylene, d-limonene, Tissue-Clear™ (believed to be an aliphatic hydrocarbon blend), and Estisol™ 220 (believed to be an ester of coconut oil).

The cover slip material was applied to glass microscope slides containing histology specimens as described above under the "Accelerated Aging Testing" section. The prepared slides were subjected to accelerated aging testing and passed the test, showing virtually no lifting of the cover slip and no fading or bleeding of the stain.

Comparative Examples D to H

Comparative Examples were made according to Horie et al. (U.S. Pat. No. 4,853,262) and tested for solvent activation properties. Comparative Examples D through H were prepared according to Examples 1a and 4a–4d of U.S. Pat. No. 4,853,262 (Horie et al.) except that the resins solutions were coated onto PET primed with polyvinylidene chloride latex primer. The coating weights of the resin layer for the Comparative Examples were about 26, 17, 14, 14, 15, and 14 gm/m$^2$, respectively.

TABLE 4

Solvent Activation Data

| | Activating Solvents | | | |
|---|---|---|---|---|
| Sample # | Xylene | D-Limonene | Tissue Clear ™ | Estisol ™ 200 |
| Example 18 | Y | Y | Y | Y |
| Example 19 | Y | Y | Y | Y |
| Example 20 | Y | Y | N | Y |
| Example 21 | Y | Y | Y | Y |
| Example 22 | Y | Y | Y | Y |
| Example 23 | Y | Y | Y | Y |
| Example 24 | Y | Y | Y | Y |
| Example 25 | Y | Y | Y | Y |
| Example 26 | Y | Y | Y | Y |
| Example 27 | Y | Y | Y | Y |
| Example 28 | Y | Y | Y | Y |
| Comparative D | Y | N | N | N |
| Comparative E | Y | N | N | N |
| Comparative F | Y | N | N | N |
| Comparative G | Y | N | N | N |
| Comparative H | Y | N | N | N |

All references cited herein are incorporated by reference, in their entirety.

What is claimed is:

1. A flexible light transmissible cover slip comprising:
   (a) a light transmissible polymeric backing having first and second surfaces;
   (b) a tack free bonding layer disposed on the first surface of the backing, the bonding layer comprising polymers selected from the group consisting of alkyl acrylate, alkyl methacrylate, and combinations thereof; and
   (c) a protective coating disposed on the second surface of the backing wherein the bonding layer is capable of being activated by an environmentally friendly solvent, wherein the environmentally friendly solvent is selected from the group consisting of terpene, d-limonene, esters of coconut oil, aliphatic hydrocarbon blends, and combinations thereof.

2. The cover slip of claim 1, wherein the backing is selected from the group consisting of polymethyl methacrylate, polyethylene, terephthalate, cellulose diacetate, cellulose triacetate, and styrene-acrylonitrile copolymer.

3. The cover slip of claim 1, wherein the alkyl acrylate is selected from the group consisting of 2-ethylhexyl acrylate, isobornyl acrylate, isooctyl acrylate, n-butyl acrylate, t-butyl acrylate, and combinations thereof, and wherein the alkyl methacrylate is selected from the group consisting of isobornyl methacrylate, and cyclohexyl methacrylate, and combinations thereof.

4. The cover slip of claim 1, wherein the bonding layer comprises octadecyl acrylate and 2-ethylhexyl acrylate at a weight ratio of about 65:35 to 90:10.

5. The cover slip of claim 1, wherein the bonding layer comprises isobornyl acrylate and 2-ethylhexyl acrylate at a weight ratio of about 65:35 to 90:10.

6. The cover slip of claim 1, wherein the bonding layer comprises cyclohexyl methacrylate and 2-ethylhexyl acrylate in a weight ratio of about 65:35 to 90:10.

7. The cover slip of claim 1, wherein the bonding layer comprises isobornyl acrylate and n-butylacrylate in a weight ratio of about 65:35 to 90:10.

8. The cover slip of claim 1, wherein the protective coating comprises polymers selected from the group consisting of silicone, fluorosilicone, fluorochemical, fluoroether, silicone acrylates, silicone epoxy, ceramer, and combinations thereof.

9. The cover slip of claim 8, wherein the protective coating comprises greater than 70% by weight ceramer and less than 30% by weight silicone acrylate.

10. The cover slip of claim 1 having a refractive index of about 1.40 to 1.60.

11. The cover slip of claim 1 further comprising gridlines disposed on the light transmissible backing.

12. The cover slip of claim 1 in roll form, the roll being exposed to a condition of about 49° C. (120° F.) for at least seven days and able to be unwind without blocking.

13. The cover slip of claim 1 disposed on a stained histology specimen microscope slide that has been exposed to xylene to yield a cover slipped slide, said cover slipped slide being exposed to an accelerated aging condition of about 49° C. (120° F.) and about 90% relative humidity for at least seven days without substantial lifting or bubbling of the cover slip material from the microscope slide and without substantial fading or bleeding of the stain.

14. A method of preparing a specimen for optical microscopy, the method comprising the steps of:
   (a) placing the specimen on a portion of a microscope slide;
   (b) applying a cover slip over the specimen and the slide, the cover slip comprising (i) an optically transparent polymeric backing having first and second surfaces; (ii) a tack free bonding layer disposed on the first surface of the backing, the bonding layer comprising polymers selected from the group consisting of alkyl acrylate, alkyl methacrylate, and combinations thereof, and (iii) a protective coating disposed on the second surface of the backing,
   (c) applying an environmentally friendly activating solvent on the cover slip, wherein the environmentally friendly activating solvent is selected from the group consisting of terpene, d-limonene esters of coconut oil, aliphatic hydrocarbon blends, and combinations thereof,
   wherein upon exposure to the activating agent, at least a portion of the bonding layer is dissolved and the cover slip adheres to the specimen and the microscope slide to yield a prepared slide.

15. The method of claim 14 further comprising applying a stain comprising hematoxylin and eosin on the specimen.

16. The method of claim 15 where said prepared slide is subjected to accelerated aging condition of about 49° C. (120° F.) at about 90% relative humidity for about seven days where said stain does not fade and/or bleed from the specimen.

17. The method of claim 14 wherein said prepared slide is subjected to accelerated aging condition of about 49° C. (120° F.) at about 90% relative humidity for about 7 days where said cover slip does not substantially lift and/or bubble.

18. The method of claim 14, wherein the acrylate is selected from the group consisting of 2-ethylhexyl acrylate, isobornyl acrylate, isooctyl acrylate, n-butyl acrylate, t-butyl acrylate, and combinations thereof, and wherein the methacrylate is selected from the group consisting of isobornyl methacrylate, and cyclohexyl methacrylate, and combinations thereof.

* * * * *